United States Patent
Assmann et al.

[11] Patent Number: 5,932,605
[45] Date of Patent: *Aug. 3, 1999

[54] SUBSTITUTED BENZIMIDAZOLES FOR PEST CONTROL

[75] Inventors: Lutz Assmann, Eutin; Albrecht Marhold, Leverkusen; Heinz-Wilhelm Dehne, Bonn; Stefan Dutzmann, Hilden; Christoph Erdelen, Leichlingen; Klaus Stenzel, Düsseldorf, all of Germany

[73] Assignee: Bayer Aktiengesellschaft, Leverkusen, Germany

[ * ] Notice: This patent is subject to a terminal disclaimer.

[21] Appl. No.: 08/972,426

[22] Filed: Nov. 18, 1997

Related U.S. Application Data

[62] Division of application No. 08/737,096, filed as application No. PCT/EP95/01536, Apr. 24, 1995, Pat. No. 5,731,300.

[30] Foreign Application Priority Data

May 6, 1994 [DE] Germany .............................. 44 16 116

[51] Int. Cl.⁶ .......................... A01N 43/90; C07F 9/6561
[52] U.S. Cl. ............................ 514/394; 514/80; 514/395; 548/111; 548/302.1
[58] Field of Search ................. 548/111, 302.1; 514/80, 394, 395

[56] References Cited

U.S. PATENT DOCUMENTS

| | | |
|---|---|---|
| 5,310,747 | 5/1994 | Enomoto et al. . |
| 5,510,364 | 4/1996 | Lunkenheimer . |
| 5,731,300 | 3/1998 | Assmann et al. ................. 548/302.1 |

*Primary Examiner*—Patricia L. Morris
*Attorney, Agent, or Firm*—Sprung Kramer Schaefer & Briscoe

[57] ABSTRACT

Novel substituted benzimidazoles of the formula

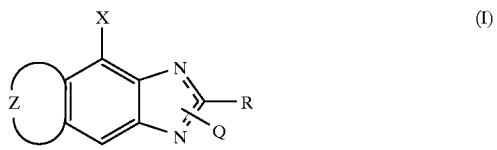

in which

Q, R, X and Z have the meanings given in the description, a process for the preparation of the novel substances and their use for combating pests.

10 Claims, No Drawings

SUBSTITUTED BENZIMIDAZOLES FOR PEST CONTROL

This application is a divisional of application Ser. No. 08/737,096, filed Oct. 30, 1996 now U.S. Pat. No. 5,731,300. Ser. No. 08/737,096 is a 371 of PCT/EP95/01536 filed Apr. 24, 1995.

The present invention relates to novel, substituted benzimidazoles, to a process for their preparation and to their use for combating pests.

It has already been disclosed that certain benzimidazole derivatives possess fungicidal and acaricidal properties (cf. DE-A 4 139 950 and EP-A 0 517 476). Thus, for example, 2-cyano-3-dimethylamninosulphonyl-6,6,7,7-tetrafluoro-[1,4]dioxino[2,3-f]-benzimidazole and 2-cyano-3-dimethylaminosulphonyl-6,6,7-trifluoro-7-chloro[1,4]dioxino-[2,3-f]-benzimidazole or 2-cyano-3-dimethylaminosulphonyl-6,7,7-trifluoro-6-chloro-[1,4]dioxino-[2,3-f]benzimidazole can be employed for combating fungi and acarids. However, the activity of these substances, especially at low application rates, is not entirely satisfactory in all cases.

Novel, substituted benzimidazoles have now been found of the formula

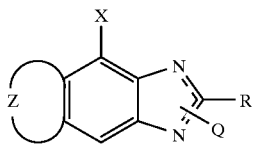

in which

R represents cyano or the groups

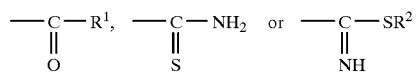

in which $R^1$ and $R^2$ independently of one another represent alkyl, alkenyl, alkinyl, halogenoalkyl or halogenoalkenyl, Q represents the groups —SO—$R^3$,

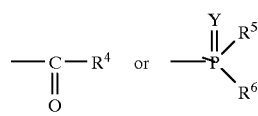

in which

Y represents oxygen or sulphur and $R^3$, $R^4$, $R^5$ and $R^6$ independently of one another represent alkyl, alkoxy, alkylthio, alkenyl, alkenyloxy, alkenylthio, alknyl, alkinyoxy, alkinylthio, amino, alkylamino, dialkylamino, optionally substituted aryl, optionally substituted aryloxy, optionally substituted arylthio, optionally substituted cycloalkyl, optionally substituted cycloalkyloxy, optionally substituted cycloalkylthio, optionally substituted cycloalkylamino, optionally substituted N-phenyl-N-alkyl-amino, optionally substituted di-cycloalkyl-amino or represent an optionally substituted, saturated or -unsaturated heterocyclic radical which is attached via nitrogen and has one nitrogen atom and 4 to 6 carbon atoms in the ring, or $R^5$ and $R^6$, together with the phosphorus atom to which they are attached, represent an optionally substituted heterocyclyl radical, X represents hydrogen or halogen and Z represents an optionally halogen-substituted alkylene chain having 3 or 4 members in which one or two (non-adjacent) carbon atoms can be replaced by oxygen atoms.

Depending on the nature of the substituents, the compounds of the formula (I) can be present as geometrical and/or optical isomers or isomer mixtures of different composition. The invention relates to both the pure isomers and the isomer mixtures.

In the formula (I) the dashed line represents a double bond between one of the two nitrogen atoms and the adjacent carbon atom which carries the substituent R.

It has additionally been found that substituted benzimidazoles of the formula (I) are obtained if benzimidazole derivatives of the formula

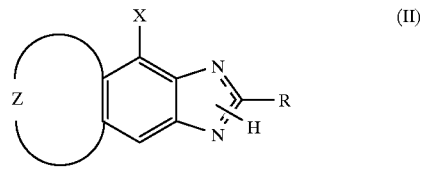

in which

R, X and Z have the meanings given above are reacted with chlorides of the formula $$Cl—Q \quad\quad (III)$$

in which

Q has the meaning given above, optionally in the presence of a diluent and optionally in the presence of a reaction auxiliary.

Finally it has been found that the substituted benzimidazoles of the formula (I) are very suitable indeed for combating pests. The substances are particularly notable for a high fungicidal, insecticidal and acaricidal activity.

Surprisingly, the substituted benzimidazoles according to the invention exhibit a better activity than 2-cyano-3-dimethylamninosulphonyl-6,6,7,7-tetrafluoro[1,4]dioxino [2,3-f]-benzimidazole, 2-eyano-3-dimethylaminosulphonyl-6,6,7-trifluoro-7-chloro-[1,4]dioxino[2,3-f]benzimidazole and 2-cyano-3-dimethylaminiosulphonyl-6,7,7-trifluoro-6-chloro-[1,4]dioxino[2,3-f]benzimidazole, which are constitutionally similar, previously known active compounds with the same general mode of action.

A general definition of the substances according to the invention is given by the formula (I).

R preferably represents cyano or represents the groups

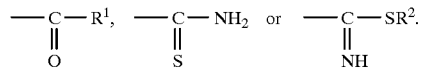

$R^1$ preferably represents straight-chain or branched alkyl having 1 to 4 carbon atoms, straight-chain or branched alkenyl having 2 to 4 carbon atoms, straight-chain or branched alkinyl having 2 to 4 carbon atoms, straight-chain or branched halogenoalkyl having 1 to 4 carbon atoms and 1 to 5 fluorine, chlorine and/or bromine atoms or represents straight-chain or branched halogenoalkenyl having 2 to 4 carbon atoms and 1 to 5 fluorine, chlorine and/or bromine atoms.

R² preferably represents straight-chain or branched alkyl having 1 to 4 carbon atoms, straight-chain or branched alkenyl having 2 to 4 carbon atoms, straight-chain or branched alkinyl having 2 to 4 carbon atoms, straight-chain or branched halogenoalkyl having 1 to 4 carbon atoms and 1 to 5 fluorine, chlorine and/or bromine atoms or represents straight-chain or branched halogenoalkenyl having 2 to 4 carbon atoms and 1 to 5 fluorine, chlorine and/or bromine atoms.

Q also preferably represents the groups —SO—R³,

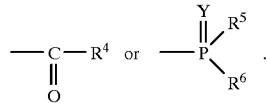

Y also preferably represents oxygen or sulphur.

R³, R⁴, R⁵ and R⁶ independently of one another preferably represent straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched alkenyl having 2 to 4 carbon atoms, straight-chain or branched alkenyloxy having 2 to 4 carbon atoms, straight-chain or branched alkenylthio having 2 to 4 carbon atoms, straight-chain or branched alkinyl having 2 to 4 carbon atoms, straight-chain or branched alkinyloxy having 2 to 4 carbon atoms, straight-chain or branched alkinylthio having 2 to 4 carbon atoms, amino, alkylamino having 1 to 4 carbon atoms, dialkylamino having 1 to 4 carbon atoms in each alkyl moiety, or represent phenyl, phenoxy or phenylthio, it being possible for each of these radicals to be substituted from one to three times by identical or different substituents consisting of fluorine, chlorine, bromine, alkyl having 1 to 4 carbon atoms, halogenoalkyl having 1 to 4 carbon atoms and 1 to 5 fluorine, chlorine and/or bromine atoms, alkoxy having 1 to 4 carbon atoms and/or halogenoalkoxy having 1 to 4 carbon atoms and 1 to 5 fluorine, chlorine and/or bromine atoms, or represent cycloalkyl having 3 to 7 carbon atoms, cycloalkloxy having 3 to 7 carbon atoms, cycloalkylthio having 3 to 7 carbon atoms, cycloalkylamnino having 3 to 7 carbon atoms, di-cycloalkylamnino having 3 to 7 carbon atoms in each cycloalkyl moiety, N-phenyl-N-alkyl-amino having 1 to 4 carbon atoms in the alkyl moiety, pyrrolidinyl, piperidinyl, pyrrolinyl, dihydropyridinyl or tetrahydropyridinyl, it being possible for each of these abovementioned radicals to be substituted from one to three times by identical or different substituents consisting of fluorine, chlorine, bromine, alkyl having 1 to 4 carbon atoms, alkoxy having 1 to 4 carbon atoms and/or halogenoalkyl having 1 to 4 carbon atoms and 1 to 5 fluorine, chlorine and/or bromine atoms.

R⁵ and R⁶ moreover, together with the phosphorus atom to which they are attached, preferably represent a 5- or 6-membered heterocyclyl radical which can include one or two further heteroatoms, such as oxygen, sulphur and/or nitrogen, and can be substituted from one to three times by identical or different substituents consisting of fluorine, chlorine, bromine, alkyl having 1 to 4 carbon atoms, alkoxy having 1 to 4 carbon atoms and/or halogenoalkoxy having 1 to 4 carbon atoms and 1 to 5 fluorine, chlorine and/or bromine atoms.

X preferably represents hydrogen, fluorine, chlorine or bromine.

Z preferably represents the groups

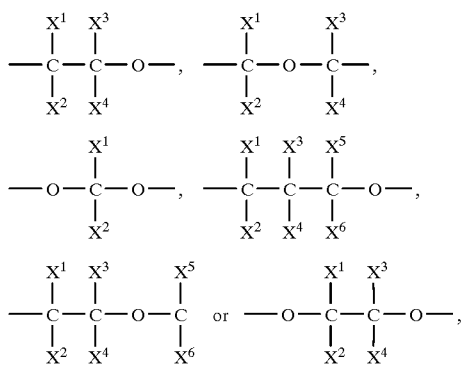

in which

X¹, X³ and X⁵ independently of one another represent hydrogen, fluorine, chlorine or bromine and X², X⁴ and X⁶ independently of one another represent fluorine, chlorine or bromine.

R is particularly preferably cyano or the groups

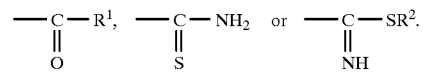

R¹ particularly preferably represents methyl, ethyl, n- or i-propyl, n-, i-, s- or t-butyl; allyl, n- or s-butenyl; propargyl, n- or s-butinyl; or represents methyl, ethyl, allyl and n- or s-butenyl each of which is substituted from one to three times by identical or different substituents consisting of fluorine and/or chlorine.

R² particularly preferably represents methyl, ethyl, n- or i-propyl, n-, i-, s- or t-butyl; allyl, n- or s-butenyl; propargyl, n- or s-butinyl; or represents methyl, ethyl, allyl and n- or s-butenyl each of which is substituted from one to three times by identical or different substituents consisting of fluorine and/or chlorine.

Q also particularly preferably represents the groups —SO—R³,

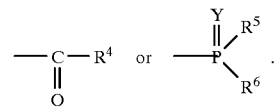

Y also particularly preferably represents oxygen or sulphur.

R³, R⁴, R⁵ and R⁶ independently of one another particularly preferably represent methyl, ethyl, n- or i-propyl, n-, i-, s- or t-butyl; methoxy, ethoxy, n- or i-propoxy, n-, i-, s- or t-butoxy; methylthio, ethylthio, n- or i-propylthio; allyl, n- or s-butenyl; allyloxy, n- or s-butenyloxy; allylthio, n- or s-butenylthio; propargyl, n- or s-butinyl; propargyloxy; propargylthio; amino; methylamnino; ethylamino, n- or i-propylamino, n-, i-, s- or t-butylamino; dimethylamino, diethylanlino, di-n- or i-propylamino, methylethylamino, methyl-n- or i-propylamino; or represent phenyl, phenoxy or phenylthio, it being possible for each of these radicals to be substituted from one to three times by identical or different substituents consisting of fluorine, chlorine, bromine, methyl, ethyl, n- or i-propyl, methoxy, ethoxy, n- or i-propoxy, trifluoromethyl and/or trifluoromethoxy, or represent cyclopropyl, cyclopentyl, cyclohexyl, cyclopropyloxy, cyclopentyloxy, cyclohexyloxy, cyclopropylthio, cyclopentylthio, cyclohexylthio, cyclopropylamino, cyclopentylamino, cyclohexylamino, di-cyclohexylamino, N-phenyl-N-alkylamino having 1 to 3 carbon atoms in the alkyl moiety, 1-pyrrolidinyl, 1-pyrrolinyl, 1-piperidinyl, 1-dihydropyridinyl and 1-tetrahydropyridinyl, it being possible for each of these radicals to be substituted from one to three times by identical or different substituents consisting of fluorine, chlorine, bromine, methyl, ethyl, n- or i-propyl, methoxy and/or trifluoromethyl.

$R^5$ and $R^6$ moreover, together with the phosphorus atom to which they are attached, particularly preferably represent a 5- or 6-membered heterocyclyl radical which can include one or two further heteroatoms such as oxygen, sulphur and/or nitrogen and can be substituted from one to three times by identical or different substituents consisting of methyl, ethyl, n- or i-propyl, methoxy, ethoxy, n- or i-propoxy, chlorine and/or trifluoromethyl, Z particularly preferably represents the groups —O—CF$_2$—O—, —O—CF$_2$—CHF—O—, —O—CHF—CHF—O—, —O—CF$_2$—CF$_2$—O—, —O—CF$_2$—CFCl—O— or —O—CFCl—CFCl—O—.

Preferred substances according to the invention are also compounds of the following formulae:

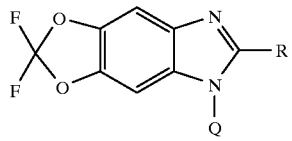
(I-A)

in which

R represents the groups —CN, —CSNH$_2$ or —COCH$_3$ and

Q represents the meanings given above.

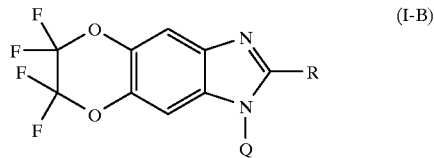
(I-B)

in which

R represents the groups —CN, —CSNH$_2$ or —COCH$_3$ and

Q represents the meanings given above.

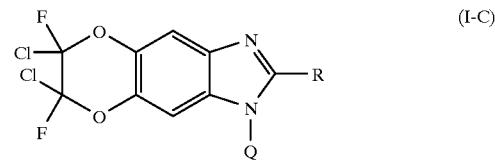
(I-C)

in which

R represents the groups —CN, —CSNH$_2$ or —COCH$_3$ and

Q represents the meanings given above.

Examples of radicals which may be mentioned for the substituent Q are as follows:

| Q | Q | Q | Q |
|---|---|---|---|
| —CO—OCH$_3$ | —SO—OCH$_3$ | —CO—CH$_3$ | —SO—CH$_3$ |
| —CO—OC$_2$H$_5$ | —SO—OC$_2$H$_5$ | —CO—C$_2$H$_5$ | —SO—C$_2$H$_5$ |
| —CO—OC$_3$H$_7$-n | —SO—OC$_3$H$_7$-n | —CO—C$_3$H$_7$-n | —SO—C$_3$H$_7$-n |
| —CO—OC$_3$H$_7$-i | —SO—OC$_3$H$_7$-i | —CO—C$_3$H$_7$-i | —SO—C$_3$H$_7$-i |
| —P(O)(SCH$_3$)(SCH$_3$) | —P(O)(OCH$_3$)(OCH$_3$) | —P(S)(OCH$_3$)(OCH$_3$) | —P(S)(OCH$_3$)(SCH$_3$) |
| —P(O)(OCH$_3$)(SCH$_3$) | —P(O)(OC$_2$H$_5$)(C$_2$H$_5$) | —P(O)(OC$_2$H$_5$)(OC$_2$H$_5$) | —P(O)(N(CH$_3$)$_2$)(N(CH$_3$)$_2$) |
| —P(S)(N(CH$_3$)$_2$)(N(CH$_3$)$_2$) | —P(O)(NHCH$_3$)(NHCH$_3$) | —P(S)(NHCH$_3$)(NHCH$_3$) | —P(O)(NHC$_2$H$_5$)(OC$_3$H$_7$-i) |
| —P(S)(NHC$_2$H$_5$)(OC$_3$H$_7$-i) | —P(S)(OC$_2$H$_5$)(OC$_6$H$_5$) | —P(O)(OC$_6$H$_5$)(OC$_6$H$_5$) | —P(O)(piperidinyl)(piperidinyl) |

-continued

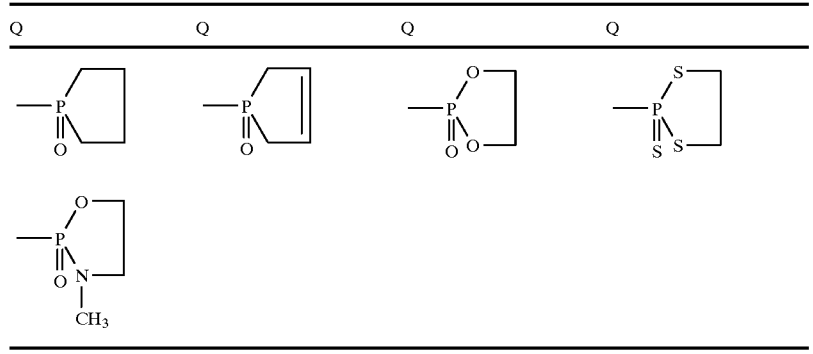

Using, for example, 2-cyano-6,6,7,7-tetrafluoro-[1,4] dioxino [2,3-f]benzimidazole and ethyl chlorosulphinate as starting materials, the course of reaction of the process according to the invention can be illustrated by the following formula scheme:

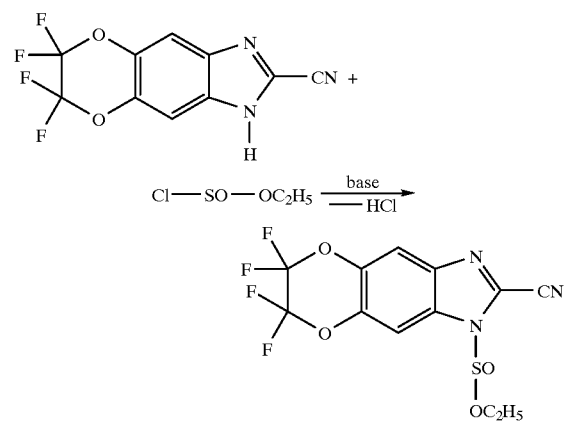

A general definition of the benzimidazole derivatives required as starting materials for carrying out the process according to the invention is given by the formula (II). In the formula (II) R, X and Z preferably or particularly preferably have those meanings which have already been given above in connection with the description of the compounds of the formula (I) as being preferred or particularly preferred for R, X and Z.

The benzimidazole derivatives of the formula (II) are known or are obtainable in a generally known manner (cf. e.g. EP-A 0 517 476, DE-A 4 139 950, FR-A 2 607 811, EP-A 0 549 943 and the Preparation Examples).

A general definition of the chlorides additionally required as starting materials for carrying out the process according to the invention is given by the formula (III). In the formula (III) Q preferably or particularly preferably has those meanings which have already been given above in connection with the description of the compounds of the formula (I) as being preferred or particularly preferred for Q.

Suitable diluents when carrying out the process according to the invention are all customary inert, organic solvents. Preferred possibilities for use are aliphatic, cycloaliphatic and aromatic, optionally halogenated hydrocarbons, for example benzine, benzene, toluene, xylene, chlorobenzene, dichlorobenzene, petroleum ether, hexane, cyclohexane, dichloromethane, chloroform or carbon tetrachloride; and, furthermore, ethers such as diethyl ether, diisopropyl ether, dioxane, tetrahydrofuran or ethylene glycol dimethyl or diethyl ether, and also ketones, such as acetone or butanone or methyl isobutyl ketone; nitriles such as acetronitrile, propionitrile or benzonitrile, or esters, such as methyl acetate or ethyl acetate.

The process according to the invention is preferably carried out in the presence of an appropriate reaction auxiliary. Suitable such auxiliaries are all customary inorganic or organic bases. Preferred possibilities for use are alkaline earth metal or alkali metal hydroxides, such as sodium hydroxide, calcium hydroxide, potassium hydroxide, or else ammonium hydroxide, alkali metal carbonates, such as sodium carbonate, potassium carbonate, potassium hydrogen carbonate, sodium hydrogen carbonate, alkali metal or alkaline earth metal acetates, such as sodium acetate, potassium acetate, calcium acetate, and also tertiary amines, such as trimethyl amine, triethyl amine, tributyl amine, N,N-dimethylaniline, pyridine, N-methylpiperidine, N,N-dimethylaminopyridine, diazabicyclooctane (DABCO), diazabicyclononene (DBN) or diazabicycloundecene (DBU).

The reaction temperatures when carrying out the process according to the invention can be varied within a relatively wide range. It is generally carried out at temperatures between 0 and 150° C., preferably at temperatures between 20 and 120° C.

The process according to the invention is usually carried out under atmospheric pressure. However, it is also possible to operate under increased or reduced pressure.

To carry out the process according to the invention, in general from 1.0 to 2.0 mol. preferably from 1.0 to 1.3 mol. of chloride of the formula (III) and optionally from 1.0 to 2.0 mol. preferably from 1.0 to 1.3 mol. of reaction auxiliary are employed per mole of benzimidazole derivative of the formula (II) in a diluent. The conduct of the reaction and the workup and isolation of the reaction products takes place in accordance with known methods (cf. also the Preparation Examples).

The active compounds of the formula (I) according to the invention have a strong action against pests and can be employed in practice for combating unwanted harmful organisms. The active compounds are suitable for use as plant protection compositions, especially as fungicides, insecticides and acaricides.

Fungicides in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum*;

Phytophthora species, such as, for example, [lacuna] Pseudoperonospora humuli or Pseudoperonospora cubensis;

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechlera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alteranara brassicae;*

Pseudocercosporella species, such as, for example, Pseudocercosporella herpotrichoides.

The fact that the active compounds are well tolerated by plants in the concentrations required for combating plant diseases permits the treatment of aerial parts of plants, of propagation stock and seeds, and of the soil.

In this context, the active compounds according to the invention can be employed with particularly good success for combating diseases in fruit growing and vegetable growing, for example against Venturia species, or for combating cereal diseases, for example against Erysiphe, Cochliobolus, Pyrenophora or Septoria species or for combating rice diseases, for example against the causative organism of rice blast disease (*Pyricularia oryzae*).

The active compounds according to the invention are, furthermore, suitable for combating animal pests, preferably arthropods and nematodes, especially insects and arachnids, which are encountered in agriculture, in forestry, in the protection of stored products and of materials, and in the hygiene field. They are active against normally sensitive and resistant species and against all or some stages of development. The abovementioned pests include: From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculate.*

From the order of the Thysanura, for example, *Lepisma saccharins.*

From the order of the Collembota, for example, *Onychiurus armatus.*

From the order of the Orthoptera, for example, *Blatta orientalis, Periplaneta americans, Leucophaea maderac, Blattella germanica, Acheta domesticus,* Gryllotalpa spp., *Locusta migratoria migratorioldes, Melanoplus differentialis* and *Schistocerca gregaria.*

From the order of the Dermaptera, for example, *Forficula auricularia.*

From the order of the Isoptera, for example, Reticulitermes spp

From the order of the Anoplura, for example, *Phylloxera vastatrix,* Pemphious spp., *Pediculus humanus corporis,* Haematopinus spp. and Linognathus spp.

From the order of the Mallophaga, for example, Trichodectes spp. and Damalinea

From the order of the T hysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neuskria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehnliella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Bruchidius obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include Pratylenchus spp., *Radopholus similis, Ditylenchus dipsaci, Tylenchulus semipenetrans*, Heterodera spp., Meloidogyne spp., Aphelenchoides spp., Longidorus spp., Xiphinema spp. and Trichodorus spp.

The active compounds of the formula (I) according to the invention are also distinguished by outstanding insecticidal action, for example against Phaedon, Spodoptera, Nephotettix and Mycus species. However, they also exhibit a good acaricidal action.

Depending on their particular physical and/or chemical properties, the active compounds can be converted into customary formulations, such as solutions, emulsions, suspensions, powders, foams, pastes, granules, aerosols, very fine capsules in polymeric substances and in coating compositions for seed, and also ULV cold mist and warm mist formulations.

These formulations are produced in a known manner, for example by mixing the active compounds with extenders, that is, liquid solvents, liquefied gases under pressure and/or solid carriers, optionally with the use of surface-active agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methyl-cellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephatins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients, such as salts of iron, manganese, boron, copper, cobalt, molybdenum and zinc.

The formulations in general contain between 0.1 and 95 per cent by weight of active compound, preferably between 0.5 and 90%.

When employed as fungicides, the active compounds according to the invention, as such or in their formulations, can also be used as a mixture with known fungicides, bactericides, acaricides, nematicides or insecticides, for example to widen the spectrum of action or to prevent the build-up of resistance. In many cases, synergistic effects are obtained, i.e. the activity of the mixture is greater than the activity of the individual components.

Examples of particularly advantageous co-components are the following compounds:

Fungicides 2-aminobutane; 2-anilino-4-methyl-6-cyclopropyl-pyrimidin; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)benzamide; (E)-2-methoximino-N-methyl-2-(2-phenoxy-phenyl)acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoxy-amino [alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflurnizole, triforine, triticonazole, validamycin A, vinclozolin, zineb, ziram Bactericides bronopol, dichlorophen, nitrapyrin, nickel dimethyldithiocarbamate, kasugamycin, octhilinone, furancarboxylic acid, oxytetr-acyclin, probenazole, streptomycin, tecloftalam, copper sulphate and other copper preparations.

Insecticides/Acaricides/Nematicides abamectin, AC 303 630, acephate, acrinathrin, alanycarb, aldicarb, alphamethrin, amitraz, avermectin, AZ 60 541, azadirachtin, azinphos A, azinphos M, azocyclotin, Bacillus thuringiensis, bendiocarb, benfuracarb, bensultap, betacyfluthrin, bifenthrin, BPMC, brofenprox, bromophos A, bufencarb, buprofezin, butocarboxin, butylpy ridaben, cadusafos, carbaryl, carbofuran, carbophenothion, carbosulfan, cartap, CGA 157 419, CGA 184 699, chloethocarb, chlorethoxyfos, chlorfenvinphos, chloriluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectirn, monocrotophos, moxidectin, naled, NC 184, NI 25, nitenpyrarn, omethoate, oxamyl, oxydemethon M, oxydeprofos, parathion A, pa-rathion M, permethrin, phenthoate, phorate, phosalone, phosmet, phosphamdon, phoxim, pirimicarb, pirimiphos M, pirimiphos A, profenofos, promecarb, propaphos, propoxur, prothiofos, prothoate, pymetrozin, pyrachlophos, pyridpetin pyemthrin, pyrethrum, pyridaben, pyrimidifen, pyriproxifen, quinalphos,

RH 5992, salithion, sebufos, silailuofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

A mixture with other known active compounds, such as herbicides, or with fertilizers and growth regulators is also possible.

When employed as fungicides, the active compounds can be applied as such, in the form of their formulations or the use forms prepared therefrom, such as ready-to-use solutions, suspensions, wettable powders, pastes, soluble powders, dusts and granules. They are applied in a customary manner, for example by pouring, coarse spraying, fine spraying, broadcasting, atomizing, foaming, brushing on, etc.

It is possible in addition to apply the active compounds by the ultra-low-volume method or to inject the preparation of active compound, or the active compound itself, into the soil. It is also possible to treat the seed of plants.

In the treatment of plant parts, the active-compound concentrations in the use forms can, when employed as fungicides, be varied within a relatively wide range. They are in general between 1 and 0.0001% by weight, preferably between 0.5 and 0.001%.

In the treatment of seed, when employed as fungicides, the quantities of active compound required are generally from 0.001 to 50 g per kilogram of seed, preferably from 0.01 to 10 g.

In treating the soil, when employed as fungicides, active-compound concentrations of from 0.00001 to 0.1% by weight, preferably from 0.0001 to 0.02%, are required at the site of action.

When employed as insecticides and acaricides, the active compounds according to the invention can be present, in their customary commercial formulations and in the use forms prepared from the formulations, as a mixture with other active compounds, such as insecticides, attractants, sterilants, acaricides, nematicides, fungicides, growth regulators or herbicides. The insecticides include, for example, phosphates, carbarnates, carboxylic esters, chlorinated hydrocarbons, phenylureas, substances produced by microorganisms, etc.

Mention may be made of the following compounds:

acrinathrin, alphamethrin, betacyfluthrin, bifenthrin, brofenprox, cis-resmethrin, clocythrin, cyclopothrin, cyfluthrin, cyhalothrin, cypermethrin, deltamethrin, esfenvalerate, etofenprox, fenpfopathrin, fenvalerate, flucythrinate, fluvalinate, lambda-cyhalothrin, permethrin, pyresmethrin, pyrethrum, silafluofen, tralomethrin, zetamethrin, alanycarb, bendiocarb, benfuracarb, bufencarb, butocarboxim, carbaryl, cartap, ethiofencarb, fenobucarb, fenoxycarb, isoprocarb, methiocarb, methomyl, metolcarb, oxamyl, pirimicarb, promecarb, propoxur, terbam, thiodicarb, thiofanox, trimethacarb, XMC, xylylcarb, acephate, azinphos A, azinphos M, bromophos A, cadusafos, carbophenothion, chlorfenvinphos, chlormephos, chlorpyrifos, chlorpyrifos M, cyanophos. Demeton M, demeton-S-methyl, demeton S, diazinon, dichlorvos, dicliphos, dichlorfenthion, dicrotophos, dimethoate, dimethylvinphos, dioxathion, disulfoton, edifenphos, ethion, etrimphos, fenitrothion, fenthion, fonophos, formothion, heptenophos, iprobenfos, isazophos, isoxathion, phorate, malathion, mecarbam, mervinphos, mesulfenphos, methacrifos, methamidophos, naled, omethoate, oxydemeton M oxydeprofos, parathion A, parathion M, phenthoate, phorate, phosalone, phosmet, phosphamdon, phoxim, pirimiphos A, pirimiphos M, propaphos, prothiophos, prothoate, pyridaphenthion, quinalphos, salithion, sebufos, sulfotep, sulprofos, tetrachlorvinphos, temephos, thiomethon, thionazin, trichlorfon, triazophos, vamidothion, buprofezin, chlorfluazuron, diflubenzuron, flucycloxuron, flufenoxuron, hexaflumuron, pyriproxifen, tebufenozide, teflubenzuron, triflumuron, imidacloprid, nitenpyram, N-[(6-chloro-3-pyridinyl) methyl]-N'-cyano-N-methylethanimide amide (NI-25), abamectin, amitrazin, avermectin, azadirachtin, bensultap, Bacillus thuningiensis, cyromazine, diafenthiuron, emamectin, ethofenprox, fenpyrad, fipronil, flufenprox, lufenuron, metaldehye, milbemectin, pymetrozine, tebufenpyrad, triazuron, aldicarb, bendiocarb, benfuracarb, carbofuran, carbosulfan, chlorethoxyfos, cloethocarb, disulfoton, ethophrophos, etrimphos, fenamiphos, fipronil, fonofos, fosthiazate, furathiocarb, HCH, isazophos, isofenphos, methiocarb, monocrotophos, nitempyram, oxamyl, phorate, phoxim, prothiofos, pyrachlofos, sebufos, silafluofen, tebupirimphos, tefluthrin, terbufos, thiodicarb, thiafenox, azocyclotin, butylpyridaben, clofentezine, cyhexatin, diafenthiuron, diethion, emamectin, fenazaquin, fenbutatin oxide, fenothiocarb, fenpropathrin, fenpyrad, fenpyroximate, fluazinam, fluazuron, flucycloxuron, flufenoxuron, fluvalinate, fubfenprox, hexythiazox, ivemectin, methidathion, monocrotophos, moxidectin, naled, phosalone, profenofos, pyridaben, pyrimidifen, tebufenpyrad, thuringiensin, triarathene and 4-bromo-2-(4-chlorophenyl)-1-(ethoxymethyl)-5-(trifluoromethyl)-1H-pyrrole-3-carbonitrile (AC 303630).

When employed as insecticides and acaricides, the active compounds according to the invention can also, in their customary commercial formulations and in the use forms prepared from these formulations, be present in a mixture with synergists. Synergists are compounds by means of which the action of the active compounds is increased without the added synergist necessarily being active itself.

The content of active compound of the use forms prepared from the customary commercial formulations can, when employed as insecticides and acaricides, vary within wide ranges. The active-compound concentration of the use forms can be from 0.0000001 up to 95% by weight of active compound, preferably between 0.0001 and 1% by weight.

Application takes place in a customary manner which is appropriate to the use forms.

The preparation and the use of the active compounds according to the invention are evident from the examples which follow.

PREPARATION EXAMPLES

Example 1

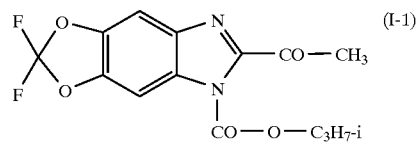

3.6 g (30 mmol) of isopropyl chloroformate are added with stirring to a mixture of 3.6 g (15 mmol) of 2-acetyl-6,6-difluoro-[1,3]dioxolo[4,5-f]benzimnidazole, 4.0 g (40 mmol) of triethylamnine and 50 ml of ethyl acetate and the mixture is heated under reflux for 18 hours. The reaction mixture is subsequently washed twice with 20 ml of water each time. The organic phase is dried and concentrated. The residue which remains is stirred with 30 ml of petroleum ether. The precipitate produced in the course of this procedure is filtered off and dried.

2.9 g (59% of theory) are obtained of 2-acetyl-6,6-difluoro-3-i-propoxycarbonyl[1,3]dioxolo[4,5-f] benzimidazole of melting point 86–89° C.

Preparation of the starting product

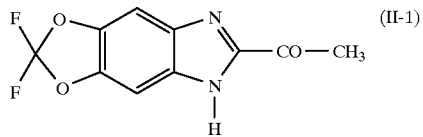

11.6 g (0.1 mol) of ethyl pyruvate are added at room temperature with stirring to a mixture of 18.8 g (0.1 mol) of 5,6-diamino-2,2-difluoro-1,3-benzodioxolane and 150 ml of ethanol and the mixture is then heated under reflux for 48 hours. The precipitate is subsequently filtered off from the cooled reaction mixture, and is washed with 30 ml of petroleum ether and dried.

16.9 g (70% of theory) are obtained of 2-acetyl-6,6-difluoro-[1,3]dioxolo[4,5-f]benzimidazole of melting point >220° C.

Example 2

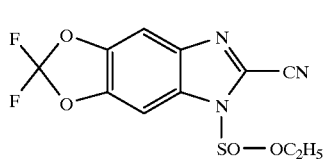

3.3 g (15 mmol) of 2-cyano-6,6-difluoro[1,3]diloxolo[4,5-f]benzimidazole are added at room temperature with stirring to a mixture of 0.45 g (15 mmol) of sodium hydride (80% pure) and 60 ml of absolute tetrahydrofuran and the mixture is then stirred at room temperature for 20 minutes. 2.5 g (20 mmol) of ethyl chztorosulphinate are subsequently added and the mixture is stirred at 60° C. for 18 hours. The reaction mixture is worked up by washing it twice with 20 ml of water each time. The organic phase is dried over sodium sulphate and concentrated under reduced pressure. The residue which remains is chromatographed on silica gel with methylene chloride as eluent.

4.0 g (85% of theory) are obtained of 2-eyano-6,6-difluoro-3-ethoxysulphinyl[1,3]-dioxolo[4,5-f] benzimidazole of melting point 173–176° C.

Example 3

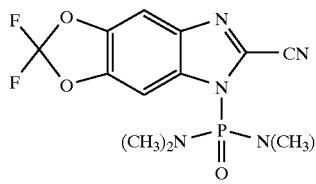

5.1 g (30 mmol) of phosphoric acid bis(dimethylamide) chloride are added to a mixture of 4.4 g (20 mmol) of 2-cyano-6,6-difluoro-[1,3]dioxolo[4,5-f]benzimidazole and 20 ml of triethylamine and the mixture is then stirred at 60° C. for 16 hours. Thereafter, the reaction mixture is poured into water and is subjected to extraction three times with 70 ml of diethyl ether each time. The combined organic extracts are dried over sodium sulphate and concentrated under reduced pressure. The residue which remains is stirred with a mixture of 5 ml of diethyl ether and 5 ml of petroleum ether. The solid which is produced in this procedure is filtered off and dried.

5.8 g (81% of theory) are obtained of 2-cyano-6,6-difluoro-3-[bis-(dimethylarnino)-phosphinyl]-[1,3]dioxolo[4,5-f]benzimidazole of melting point 90–93° C.

In a corresponding manner and in accordance with the general preparation instructions, the following benzimidazoles are obtained of the formula

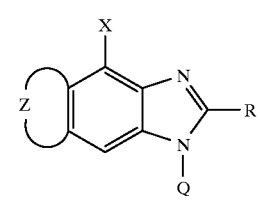

| Ex. No.: | R | Q | X | Z | m.p. 87–89° C. Physical constant |
|---|---|---|---|---|---|
| 4 | —CN | —CO—OC$_3$H$_7$-i | H | —OCF$_2$O— | m.p. 87–89° C. |
| 5 | —CN | —CO—OC$_3$H$_7$-i | H | —OCFClCFClO— | $^1$H-NMR(CDCl$_3$) 1.59(d, 6H); 5.38–5.47(dq, 1H) 7.65(s, 1H); 7.92(s, 1H) |
| 6 | —CN | —CO—OC$_3$H$_7$-i | H | —OCF$_2$CF$_2$O— | m.p. 77–82° C. |
| 7 | —CN | —CO—OCH$_3$ | H | —OCF$_2$CF$_2$O— | m.p. 150–155° C. |
| 8 | —COCH$_3$ | —CO—OC$_3$H$_7$-i | H | —OCFClCFClO— | m.p. 96–99° C. |
| 9 | —COCH$_3$ | —CO—OC$_3$H$_7$-i | H | —OCF$_2$CF$_2$O— | m.p. 90–93° C. |
| 10 | —COCH$_3$ | —CO—N(CH$_3$)$_2$ | H | —OCF$_2$O— | m.p. 136–140° C. |
| 11 | —CN | —CO—N(CH$_3$)$_2$ | H | —OCF$_2$O— | m.p. 182–187° C. |
| 12 | —CN | —CO—N(CH$_3$)$_2$ | H | —OCF$_2$CF$_2$O— | m.p. 140–144° C. |
| 13 | —COCH$_3$ | —P(O)(N(CH$_3$)$_2$)$_2$ | H | —OCF$_2$CF$_2$O— | m.p. 132–134° C. |

-continued

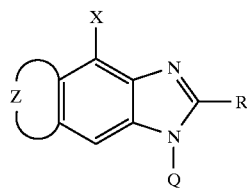

(I)

| Ex. No.: | R | Q | X | Z | m.p. 87–89° C. Physical constant |
|---|---|---|---|---|---|
| 14 | —CN | —P(O)(N(CH₃)₂)₂ | H | —OCFClCFClO— | m.p. 80–84° C. |
| 15 | —CN | —P(O)(N(CH₃)₂)₂ | H | —OCF₂CF₂O— | m.p. 72–75° C. |
| 16 | —C(=S)—NH₂ | —P(O)(piperidino)₂ | H | —O—CF₂—O— | m.p. 100° C. |
| 17 | —CN | —P(O)(OC₂H₅)₂ | H | —O—CF₂—O— | m.p. 129–133° C. |
| 18 | —C(=O)—CH₃ | —C(=O)—N(CH₃)₂ | H | —O—CF₂—CF₂—O— | m.p. 110–113° C. |
| 19 | —CN | —C(=O)—N(CH(CH₃)₂)(3,4-dimethoxyphenyl) | H | —O—CF₂—CF₂—O— | m.p. 107° C. |
| 20 | —CN | —P(S)(OC₂H₅)₂ | H | —O—CF₂—CF₂—O— | ¹H-NMR(DMSO) δ = 1.23(t, 6H), 3.93(q, 4H), 7.94 (s, 2H) |

Use Examples

In the following Use Examples, the compounds listed below were employed as comparison substances.

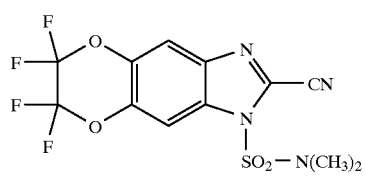

(A)

2-cyano-3-dimethylaminosulphonyl-6,6,7,7-tetrafluoro-[1,4]dloxino[2,3-f]benzimidazole

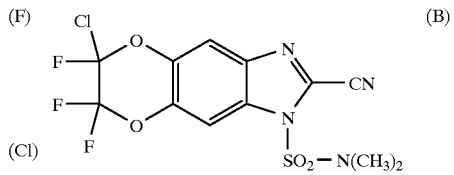

(B)

2-cyano-3-dimethylaminosulphonyl-6,6,7 (or 6,7,7)-trifluoro-7 (or 6, respectively)-chloro-[1,4]dloxino[2,3-f]benzimidazole (Both known from EP-A 0 517 476 and DE-A 4 139 950, respectively.) cl Example A Venturia test (apple)/protective Solvent: 4.7 parts by weight of acetone Emulsifier: 0.3 parts by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism Venturia inaequalis and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

At an application rate of 10 ppm, the compound according to Example 5 shows a degree of action of more than 60% while the comparison substances (A) and (B) have a degree of action of 43 and 18% respectively.

Example B

Erysiphe test (barley)/protective

Solvent: 10 parts by weight of N-methyl-pyrrolidone

Emulsifier: 0.6 parts by weight of alkyl-aryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are dusted with spores of *Erysiphe graminis* f.sp. *hordel*.

The plants a-re placed in a greenhouse at a temperature of about 20° C. and a relative atmospheric humidity of about 80%, in order to promote the development of powdery mildew fungi.

Evaluation is carried out 7 days after the inoculation.

At an application rate of 125 g/ha, the compound according to Example 15 shows a degree of action of 100% while the comparison substances (A) and (B) have a degree of action of 83%.

TABLE A

Venturia test (apple)/protective

| Active compound | | Degree of action in % of the untreated control at an active-compound concentration of 10 ppm |
|---|---|---|
| 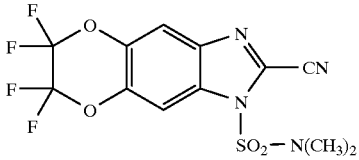 | (A) (known) | 43 |
| 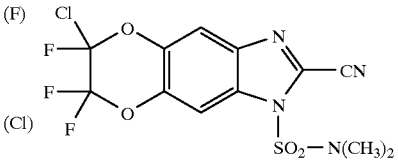 | (B) (known) | 18 |
| According to the invention 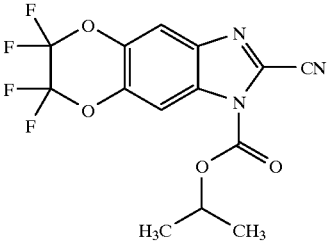 | (5) | 65 |

60

TABLE B

Erysiphe test (barley)/protective

| Active compound | | Degree of action in % of the untreated control at an active-compound concentration of 125 g/ha |
|---|---|---|
| 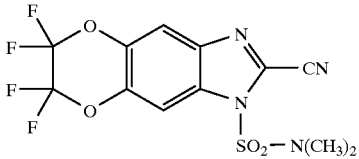 | (A) (known) | 83 |
| 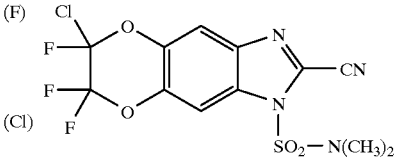 | (B) (known) | 83 |
| According to the invention 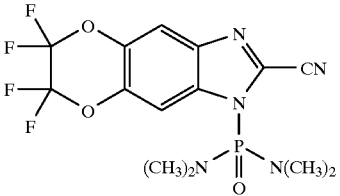 | (15) | 100 |

Example C
Erysiphe test (wheat)/protective

Solvent: 10 parts by weight of N-methyl-pyrrolidone

Emulsifier: 0.6 parts by weight of alkyl-aryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are dusted with spores of *Erysiphe graminis* f.sp. *tritici*.

The plants are placed in a greenhouse at a temperature of about 20° C. and a relative atmospheric humidity of about 80%, in order to promote the development of powdery mildew pustules.

Evaluation is carried out 7 days after the inoculation.

At an application rate of 125 g/ha, the compound according to Example 15 shows a degree of action of 75% while the comparison substances (A) and (B) have a degree of action of 25%.

TABLE C

Erysiphe test (wheat)/protective

| Active compound | | Degree of action in % of the untreated control at an active-compound concentration of 125 g/ha |
|---|---|---|
| 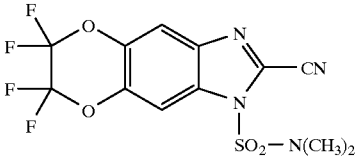 | (A) (known) | 25 |

TABLE C-continued

Erysiphe test (wheat)/protective

| Active compound | | Degree of action in % of the untreated control at an active-compound concentration of 125 g/ha |
|---|---|---|
| 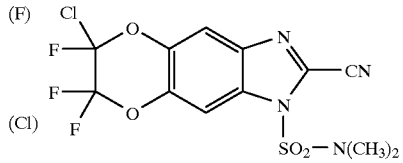 | (B) (known) | 25 |
| According to the invention | | |
| 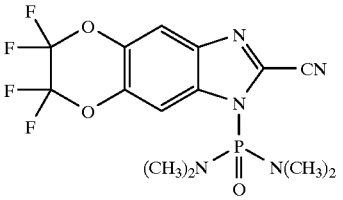 | (15) | 75 |

Example D

Phaedon larvae test

Solvent: 7 parts by weight of dimethylformamide

Emulsifier: 1 parts by weight of alkyl-aryl polyglycol ether

To produce a suitable preparation of active compound, 1 part by weight of active compound is mixed with the stated amounts of solvent, and the concentrate is diluted with water and the stated amount of emulsifier to the desired concentration.

Cabbage leaves (*Brassica oleracea*) are treated by being dipped into the preparation of active compound of the desired concentration and are infested with mustard beetle larvae Phaedon cochleariae while the leaves are still moist.

After the desired time, the degree of destruction in % is determined. 100% means that all the beetle larvae have been killed; 0% means that no beetle larvae have been killed.

In this test, the compound according to Preparation Example 3 at an active-compound concentration of 0.001% shows after 7 days a degree of destruction of 100% while the comparison substances (A) and (B) have no action.

TABLE D

Phaedon larvae test

| Active compound | | Active-compound concentration in % | Degree of destruction in % after 7 days |
|---|---|---|---|
| 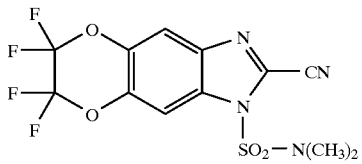 | (A) (known) | 0.001 | 0 |
| 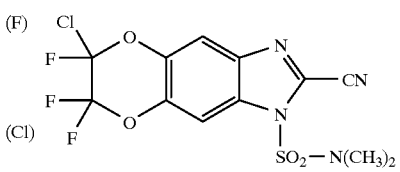 | (B) (known) | 0.001 | 0 |

TABLE D-continued

Phaedon larvae test

| Active compound | | Active-compound concentration in % | Degree of destruction in % after 7 days |
|---|---|---|---|
| According to the invention 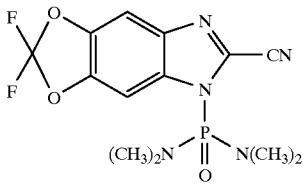 | (3) | 0.001 | 100 |

Example E

Spodoptera test

Solvent: 7 parts by weight of dimethylformamnide

Emulsifier: 1 parts by weight of alkyl-aryl polyglycol ether

To produce a suitable preparation of active compound, 1 part by weight of active compound is mixed with the stated amounts of solvent, and the concentrate is diluted with water and the stated amount of emulsifier to the desired concentration.

Cabbage leaves (*Brassica oleracca*) are treated by being dipped into the preparation of active compound of the desired concentration and are infested with caterpillars of the owlet moth Spodoptera frugiperda while the leaves are still moist.

After the desired time, the degree of destruction in % is determined. 100% means that all the caterpillars have been killed; 0% means that no caterpillars have been killed.

In this test, the compound according to Preparation Example 14 at an active-compound concentration of 0.01% shows after 3 days a degree of destruction of 100% while the comparison substances (A) and (B) have a degree of action of 10% and 0% respectively.

TABLE E

Spodoptera test

| Active compound | | Active-compound concentration in % | Degree of destruction in % after 3 days |
|---|---|---|---|
| 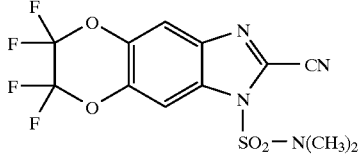 | (A) (known) | 0.01 | 10 |
| (F) (Cl) 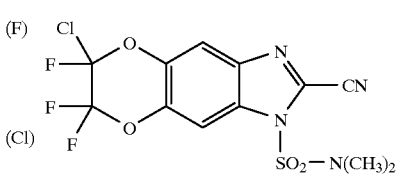 | (B) (known) | 0.01 | 0 |
| According to the invention 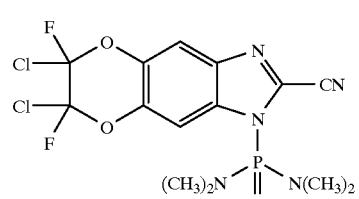 | (14) | 0.01 | 100 |

Example F

Nephotettix test

Solvent: 7 parts by weight of dimethylformamide

Emulsifier: 1 parts by weight of alkyl-aryl polyglycol ether

To produce a suitable preparation of active compound, 1 part by weight of active compound is mixed with the stated amounts of solvent, and the concentrate is diluted with water and the stated amount of emulsifier to the desired concentration.

Rice seedlings (*Oryza sativa*) are treated by being dipped into the preparation of active compound of the desired concentration and are infested with the green rice leafhopper Nephotettlx cincticeps while the leaves are still moist.

After the desired time, the degree of destruction in % is determined. 100% means that all the leafhoppers have been killed; 0% means that no leafhoppers have been killed.

In this test, the compounds according to Preparation Examples 3 and 15 at an active-compound concentration of 0.01% show after 6 days a degree of destruction of 100% while the comparison substances (A) and (B) have no action.

Example G

Myzus test

Solvent: 7 parts by weight of dimethylformamide

Emulsifier: 1 parts by weight of alkyl-aryl polyglycol ether

To produce a suitable preparation of active compound, 1 part by weight of active compound is mixed with the stated amounts of solvent and the stated amount of emulsifier, and the concentrate is diluted with water to the desired concentration. Cabbage leaves (*Brassica oleracca*) which are heavily infested by the peach aphid (*Myzus persicae*) are treated by being dipped into the preparation of active compound of the desired concentration.

After the desired time, the degree of destruction in % is determined. 100% means that all the aphids have been killed; 0% means that no aphids have been killed.

In this test, the compound according to Preparation Example 3 at an active-compound concentration of 0.1% shows after 6 days a degree of destruction of 90% while the comparison substances (A) and (B) have no action.

TABLE F

Nephotettix test

| Active compound | | Active-compound concentration in % | Degree of destruction in % after 6 days |
|---|---|---|---|
| [Structure with F, O, N, CN, $SO_2-N(CH_3)_2$ groups] | (A) (known) | 0.001 | 0 |
| (F)(Cl) [Structure with Cl, F, O, N, CN, $SO_2-N(CH_3)_2$ groups] | (B) (known) | 0.001 | 0 |
| According to the invention | | | |
| [Structure with F, O, N, CN, $(CH_3)_2N-P(=O)-N(CH_3)_2$ groups] | (3) | 0.001 | 100 |
| [Structure with F, F, F, F, O, N, CN, $(CH_3)_2N-P(=O)-N(CH_3)_2$ groups] | (15) | 0.01 | 100 |

TABLE G

Myzus test

| Active compound | Active-compound concentration in % | Degree of destruction in % after 6 days |
|---|---|---|
| 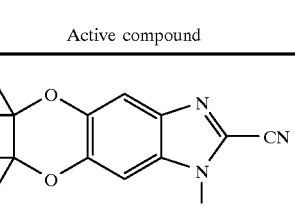 (A) (known) | 0.1 | 0 |
| 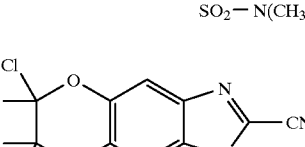 (B) (known) | 0.1 | 0 |
| According to the invention 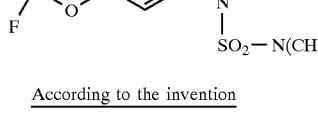 (3) | 0.1 | 90 |

We claim:

1. A substituted benzimidazole compound of the formula (I):

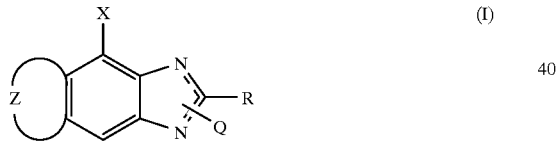

in which

R represents cyano, —CO—$R^1$, —CS—$NH_2$ or —C(NH)—$SR^2$;

in which $R^1$ represents straight-chain or branched alkyl having 1 to 4 carbon atoms, straight-chain or branched alkenyl having 2 to 4 carbon atoms, straight-chain or branched alkynyl having 2 to 4 carbon atoms, straight-chain or branched halogenoalkyl having 1 to 4 carbon atoms and 1 to 5 halogen atoms independently selected from the group consisting of fluorine, chlorine and bromine atoms, or straight-chain or branched halogenoalkenyl having 2 to 4 carbon atoms and 1 to 5 halogen atoms independently selected from the group consisting of fluorine, chlorine and bromine atoms;

$R^2$ represents straight-chain or branched alkyl having 1 to 4 carbon atoms, straight-chain or branched alkenyl having 2 to 4 carbon atoms, straight-chain or branched alkynyl having 2 to 4 carbon atoms, straight-chain or branched halogenoalkyl having 1 to 4 carbon atoms and 1 to 5 halogen atoms independently selected from the group consisting of fluorine, chlorine and bromine atoms, or straight-chain or branched halogenoalkenyl having 2 to 4 carbon atoms and 1 to 5 halogen atoms independently selected from the group consisting of fluorine, chlorine and bromine atoms;

Q represents —CO—$R^4$;

in which $R^4$ represents straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched alkenyl having 2 to 4 carbon atoms, straight-chain or branched alkenyloxy having 2 to 4 carbon atoms, straight-chain or branched alkenylthio having 2 to 4 carbon atoms, straight-chain or branched alkynyl having 2 to 4 carbon atoms, straight-chain or branched alkynyloxy having 2 to 4 carbon atoms, straight-chain or branched alkynylthio having 2 to 4 carbon atoms, amino, alkylamino having 1 to 4 carbon atoms, or dialkylamino having 1 to 4 carbon atoms in each alkyl moiety; or represents phenyl, phenoxy or phenylthio, each of which is optionally substituted one to three times by identical or different substituents selected from the group consisting of fluorine, chlorine, bromine, alkyl having 1 to 4 carbon atoms, halogenoalkyl having 1 to 4 carbon atoms and 1 to 5 halogen atoms independently selected from the group consisting of fluorine, chlorine and bromine atoms, and halogenoalkoxy having 1 to 4 carbon atoms and 1 to 5 halogen atoms independently selected from the group consisting of fluorine, chlorine and bromine atoms; or represents cycloalkyl having 3 to 7 carbon atoms, cycloalkyloxy having 3 to 7 carbon atoms, cycloalkylthio having 3 to 7 carbon atoms, cycloalkylamino having 3 to 7 carbon atoms, dicycloalkylamino having 3 to 7 carbon atoms in each cycloalkyl moiety, or N-phenyl-N-alkylamino having 1 to 4 carbon atoms in the alkyl moiety;

X represents hydrogen, fluorine, chlorine or bromine; and

Z represents a group having the formula:

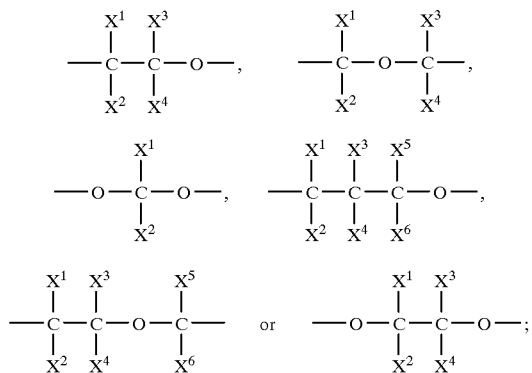

in which $X^1$, $X^3$ and $X^5$ independently represent hydrogen, fluorine, chlorine or bromine; and $X^2$, $X^4$ and $X^6$ independently represent fluorine, chlorine or bromine.

2. A substituted benzimidazole compound according to claim 1, which has the formula:

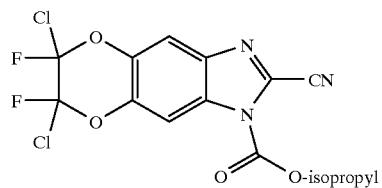

3. A composition comprising a substituted benzimidazole compound according to claim 1 and an inert diluent.

4. A composition comprising a substituted benzimidazole compound according to claim 2 and an inert diluent.

5. A method for combating fungi, which method comprises applying to said fungi or to their habitat a fungicidally effective amount of a substituted benzimidazole compound according to claim 1.

6. A method for combating fungi, which method comprises applying to said fungi or to their habitat a fungicidally effective amount of a substituted benzimidazole compound according to claim 2.

7. A method for combating insects, which method comprises applying to said insects or to their habitat an insecticidally effective amount of a substituted benzimidazole compound according to claim 1.

8. A method for combating insects, which method comprises applying to said insects or to their habitat an insecticidally effective amount of a substituted benzimidazole compound according to claim 2.

9. A method for combating acarids, which method comprises applying to said acarids or to their habitat an acaricidally effective amount of a substituted benzimidazole compound according to claim 1.

10. A method for combating acarids, which method comprises applying to said acarids or to their habitat an acaricidally effective amount of a substituted benzimidazole compound according to claim 2.

* * * * *